United States Patent [19]

Yamamoto et al.

[11] Patent Number: 4,786,165
[45] Date of Patent: Nov. 22, 1988

[54] FLOW CYTOMETRY AND APPARATUS THEREFOR

[75] Inventors: Hiroshi Yamamoto; Atsuo Tomioka, both of Hyogo, Japan

[73] Assignee: TOA Medical Electronics Co., Ltd., Kobe, Japan

[21] Appl. No.: 10,777

[22] Filed: Feb. 4, 1987

[30] Foreign Application Priority Data

Jul. 10, 1986 [JP] Japan .................. 61-238827

[51] Int. Cl.⁴ .................. G01P 3/40; G01N 33/48
[52] U.S. Cl. .................. 356/23; 356/39; 382/6
[58] Field of Search .................. 356/23, 39, 72, 73; 382/6; 350/431

[56] References Cited

U.S. PATENT DOCUMENTS

| | | | |
|---|---|---|---|
| 4,070,113 | 1/1978 | Frazer et al. | 356/39 X |
| 4,155,630 | 5/1979 | Ih | 350/431 |
| 4,338,024 | 7/1982 | Bolz et al. | 356/39 X |
| 4,395,397 | 7/1983 | Shapiro | 356/36 X |

Primary Examiner—Vincent P. McGraw
Attorney, Agent, or Firm—Pearne, Gordon, McCoy & Granger

[57] ABSTRACT

A method and apparatus for flow cytometry in which laser light pulses are focused on a sheathed stream, a still picture of cells passing by the region of the focal point is taken by an objective lens-CCD camera combination, the still picture obtained is processed and analyzed to acquire information relating to the shape and internal state of individual cells, and the cells are subjected to analysis based on the information acquired.

2 Claims, 6 Drawing Sheets

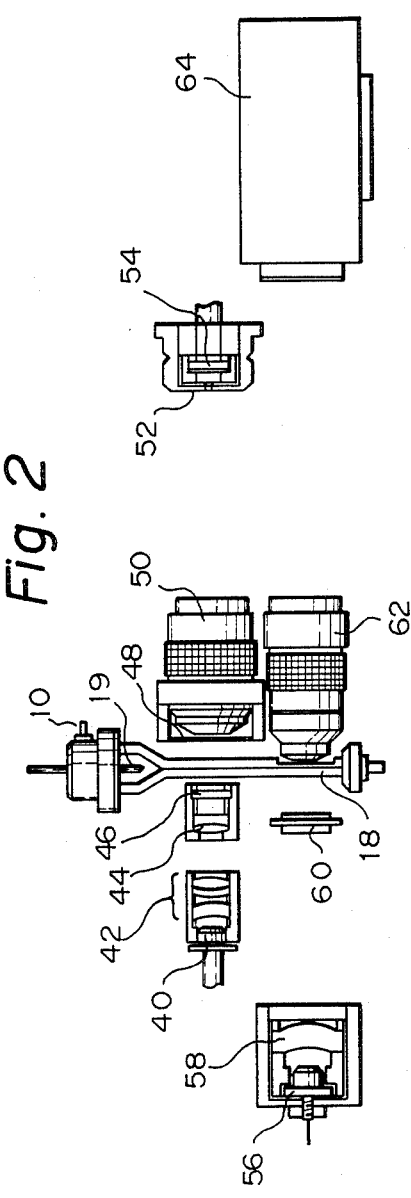
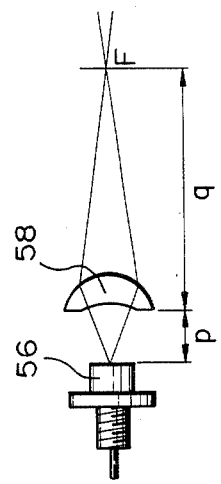
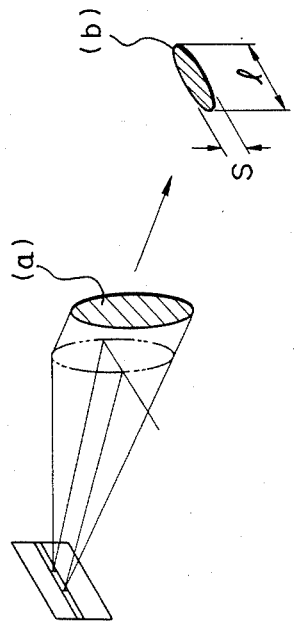

FLOW CYTOMETRY AND APPARATUS THEREFOR

BACKGROUND OF THE INVENTION

This invention relates to flow cytometry of the type in which a still picture of cells such as hemocytes in a flow of liquid is obtained and analyzed. The invention also pertains to an apparatus for practicing flow cytometry of this kind.

The conventional method of examining cells entails staining a smear of the cells on a glass slide and observing the cells under a microscope. Two problems are encountered in practicing this method. First, before the cells are observed under the microscope, it is required that a complicated procedure which includes smearing, fixing and staining the cells be followed to prepare the sample. Second, whereas cells such as hemocytes are present in a flowing liquid such as the blood when in a living body, with the conventional method these cells can only be observed in the fixed state and therefore do not present a true indication of the original cell morphology.

Recently, several attempts have been made to photograph the microscopical image of particles in a flow. For example, V. Kachel, et al., *The Journal of Histochemistry and Cytochemistry*, vol. 27, No. 1, p. 335 (1979) describe a method in which a still picture of particles is obtained by transmitting a suspension of the particles through an orifice, sensing the transmission of the particles through the orifice by a variation in electrical impedance at such time, triggering a flash lamp at the instant the particles are sensed and simultaneously photographing the particles. Further, the specifications of Japanese Patent Publication (KOKOKU) No. 57-500995 and Japanese Patent Application Laid-Open (KOKAI) No. 58-76740 teach a method of obtaining a still picture of particles in a liquid flow by passing a liquid specimen through a passageway, triggering a strobe at a fixed cycle in an imaging region and simultaneously photographing the particles with a CCD camera.

These attempts at photographing the microscopical image of particles in a flow involve a number of problems and shortcomings. The Kachel method requires the combining of resistive and optical detection principles and therefore necessitates a detector set-up which is structurally complex and difficult to adjust. Likewise, the method disclosed in Japanese Patent Publication No. 57-500995 relies upon a structurally complicated flow cell for forming the imaging region, and additional complications are encountered in producing the specimen flow. Furthermore, both methods use a flash lamp or strobe light known to emit an irradiating light pulse of comparatively large pulse width. In order to obtain a still picture, therefore, the flow velocity of the specimen carrying the particles of interest cannot be made very high. This places a limitation upon the processing capability of the system.

Neither of the aforementioned methods deals with image analysis of the internal cell structure and with the utilization of the information that might be obtained. Thus, these methods not only are incapable of making genuine cytometry possible but are not designed for such purpose.

SUMMARY OF THE INVENTION

An object of the present invention is to provide a method of analyzing cells in a flow whereby a still picture of cells in a flow can be obtained, the picture analyzed to obtain information relating to the shape and internal state of the cells, and the information utilized to make a correct cell identification, all through a set-up which is structurally simple and easy to maintain and adjust.

Another object of the present invention is to provide an apparatus for practicing the aforementioned method.

According to the present invention, the first object is attained by providing a method of flow cytometry comprising the steps of forming the focal point of a laser light beam, which is emitted by an image pick-up laser pulse light source, on a portion of a sheathed stream through which cells flow, irradiating cells which flow by the region of the focal point with the laser light beam, taking a still picture of the cells with an objective lens and a CCD camera, processing and analyzing the still picture obtained, and analyzing the cells based on information relating to the shape and internal state of the cells whose still picture has been analyzed.

According to the present invention, the second object is attained by providing an apparatus for flow cytometry comprising a flow cell through which a sheathed stream flows, an image pick-up laser pulse light source, a condenser lens for condensing laser light emitted by the image pick-up laser pulse light source, an objective lens and a CCD camera for taking a still picture of cells flowing through the sheathed stream when the cells are illuminated by the condensed laser light, and a picture processor for processing and analyzing the still picture obtained. In a preferred embodiment of the invention, the apparatus further comprises a triggering light source which emits light at all times, a cell sensor for generating a cell detection signal upon sensing that a cell has traversed a light beam from the triggering light source, and a delay circuit for transmitting the cell detection signal to the image pick-up laser pulse light source after delaying the cell detection signal for a fixed period of time. A member for reducing the coherence of the image pick-up laser pulse may be arranged between the condenser lens and the photo cell.

The light emitted by the photographic laser pulse light source has a pulse width that is greatly reduced so that a still picture can be obtained of the cells in the flow. Moreover, the still picture of cells so obtained is submitted to analysis to acquire information concerning cell configuration and internal state. This information is utilized to correctly identify and analyze the cells photographed so that precise cytometry can be realized on-line.

The present invention has the following advantages:

(1) Since a laser pulse light source is used, the pulse width can be made very small. This makes it easy to obtain a still picture of cells in a flow.

(2) Information relating to the shape and internal state of a cell can be obtained by analyzing the still picture.

(3) The morphology of cells when they are in a flowing state can be observed directly. The morphological information thus obtained cannot be acquired by microscopic observation of cells on a glass slide.

(4) The flow cell used in the apparatus is of a very simple prismatic configuration and therefore is readily manufactured. If passage of cells through the flow cell is to be detected and the light emitted from the image pick-up laser pulse light source is to be controlled, it will suffice to provide an optical system for cell detection above the image pick-up optical system. The apparatus of the invention therefore is very simple in structure and easy to manufacture, maintain and adjust.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 2 is a view useful in describing an optical system in an embodiment employing a semiconductor laser in the apparatus for flow cytometry according to the present invention;

FIG. 3 is a perspective view illustrating a light radiation pattern in a cell sensing system shown in FIG. 2;

FIG. 4 is a view useful in describing an enlargement optical system on the side of a photographic light source shown in FIG. 2;

DETAILED DESCRIPTION

Figure 1:
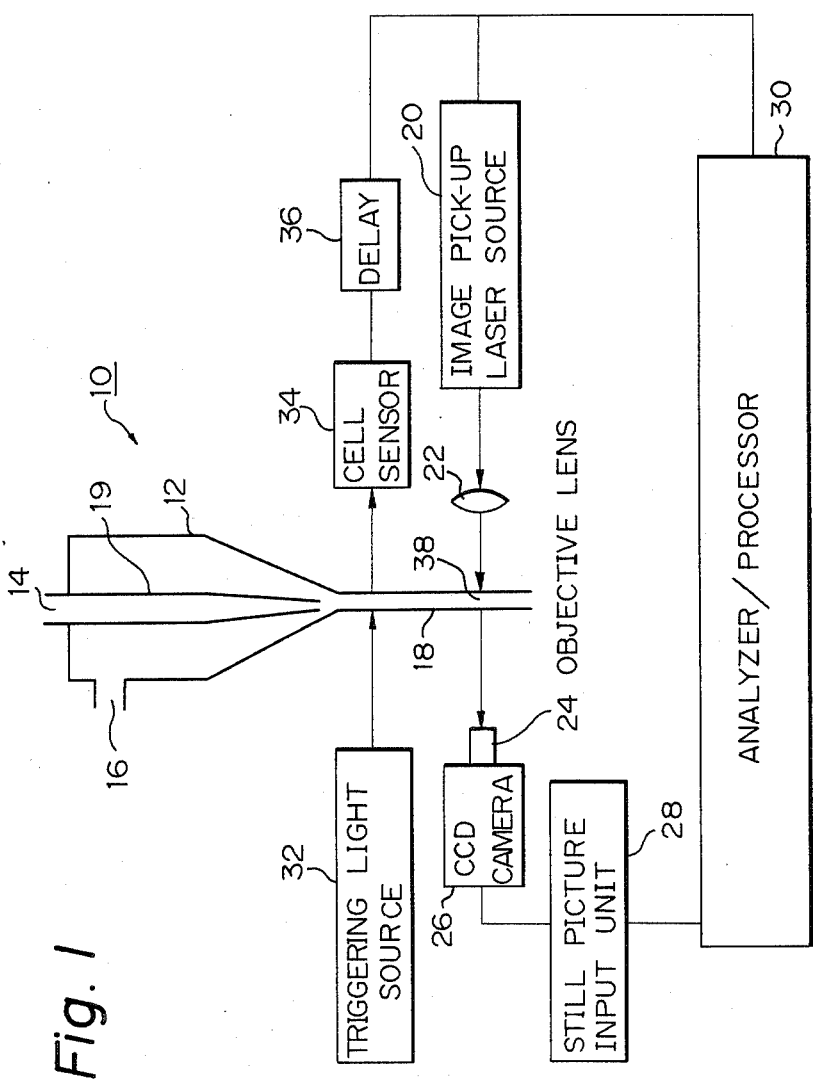
FIG. 1 is a block diagram illustrating an embodiment of an apparatus for practicing flow cytometry in accordance with the present invention.

An embodiment of the present invention will now be described in detail with reference to FIG. 1.

An apparatus 10 for flow cytometry in accordance with the invention includes a chamber 12 the upper part of which has an inlet 14 for supplying a liquid specimen in which cells are floating freely in a diluent or dye solution. Also provided at the upper part of the chamber 12 in the side wall thereof is an inlet 16 from which a physiologic saline solution or distilled water (hereafter referred to as a "sheathing" solution) is supplied.

The liquid specimen and sheathing solution flow downwardly within the chamber 12 and reach a flow cell 18 of prismatic shape. Within the flow cell 18 the liquid specimen flows in a state where it is enveloped by the sheathing solution. This is referred to as a "sheathed" stream or flow.

The optical system used in the illustrated embodiment relies upon a nitrogen laser, semiconductor laser or YAG laser as an image pick-up laser pulse light source 20. The light beam from the light source 20 advances in the direction indicated by the arrow. The light emitted by the light source 20 is focused by a condenser lens 22 in such a manner that the focal point is formed at a position on the flow cell 18 through which the sheathed liquid specimen flows. Hereafter, this position shall be referred to as an "imaging point", indicated by numeral 38. The laser light which passes through the flow cell 18 is incident upon an objective lens 24.

When a cell in the liquid specimen passes by the imaging point 38, the overall image of the cell is picked up by a CCD camera 26 when the laser pulse is emitted by the source 20. The CCD camera 26 sends the picture of the cell to a still picture input unit 28, which inputs the signal to a system controller and picture analyzer 30, where the picture is processed and analyzed.

A triggering light source 32 is adapted to illuminate the flow cell 18 at all times so that the passage therethrough of a cell may be sensed by a cell sensor 34, the latter responding by producing a pulse signal when the cell is sensed. A delay circuit 36 delays the pulse signal for a fixed period of time, during which the cell is capable of being photographed by the emission of the laser pulse from the laser pulse light source 20. The purpose of the delay circuit 36 is to delay the emission of the laser pulse from the laser pulse light source 20 for a time corresponding to the velocity of the flow through the flow cell, namely for a period of time from detection of the cell by the cell sensor 34 until the cell reaches the imaging point 38. Since the pulse width of the signal outputted by the cell sensor 34 will differ depending upon the size of the cell sensed, the cells in the liquid specimen flow can be sensed selectively by arranging it so that the light source 20 emits the laser pulse only when cells having the size of interest are sensed. It should be noted that if the light source 20 is adapted to emit laser light continuously at a fixed cycle, the probability that cells will be photographed will correspond to the concentration of the cells present in the liquid specimen flow. The system controller and picture analyzer 30 is adapted to control the overall operation of the apparatus 10.

Let us now describe the triggering light source 32 and cell sensor 34 in detail with reference to FIG. 2.

In a preferred embodiment of the invention as shown in FIG. 2, the flow cell 18 has a rectangular transverse cross section, a thickness of about 0.3 mm at the thinnest portion perpendicular to the optical axis, an inner diameter of 0.1 to 0.5 mm on one side and 0.2 to 1 mm on the other side. These dimensions can be varied in dependence upon the specimen to be analyzed. The flow cell 18 includes a nozzle 19 for injecting the specimen. The nozzle 19 has an inner diameter of 0.2 to 0.5 mm.

Numeral 40 denotes a semiconductor laser for emitting visible light, the power of the laser being 2 to 20 mW. The semiconductor laser 40 is provided with a collimator lens 42 which can be of the type available on the market for use in optical disk devices. The lens 42 has a numerical aperture NA of 0.45 to 0.6 and outputs parallel light whose beam cross section is elliptical in shape. A condenser lens 44 has an F number of less than 30 and a focal length f of more than 10 mm. The condenser lens 44 is provided with a fine position adjuster (not shown) by which the position of the lens is adjusted in such a manner that its focal point may be formed near the center of the flow cell 18. A cylinder lens 46 acts to stop a light radiation pattern having the cross sectional shape shown at (a) of FIG. 3 down to a pattern having the cross section depicted at (b) of FIG. 3. The S dimension of the cross section shown at (b) of FIG. 3 is decided by the F number of the condenser lens 44, and the l dimension is decided by the amount of astigmatism attributable to the cylinder lens 46. Suitable values for cell detection are S=7-20 um, l=10-300 um. The semiconductor laser 40, collimator lens 42, condenser lens 44 and cylinder lens 46 constitute the aforementioned triggering light source 32 shown in FIG. 1.

A beam stopper 48 acts to block direct light and transmit forward-scattered light over a range of two degrees or more with respect to the optical axis. It is known that the intensity of forward-scattered light over such a small angle is reflective of cell size. A collector lens 50 receives the light from the beam stopper 48 and comprises a lens having the low magnification of a microscope objective lens, namely a magnification of 4 to 20. The collector lens 50 serves to focus the forward-scattered light at the center of a pin hole 52. The latter has a diameter selected between 0.2 and 2 mm depending upon magnification and the thickness of the photo cell 18. Both the collector lens 50 and pin hole 52 have their positions adjusted by fine position adjusters (not shown). The distance from the collector lens 50 to the pin hole 52 is about 150 mm if an objective lens for a biological microscope is employed as the collector lens 50, and about 200 mm if an objective lens for a metallurgical microscope is used as the collector lens 50. The distance between the collector lens 50 and pin hole 52 is adjusted in dependence upon the distance between the flow cell 18 and the collector lens 50.

Numeral 54 denotes a photodiode or pin photodiode. A reverse biasing voltage is impressed upon the photodiode or pin photodiode 54 to reduce its junction capacitance, thereby raising the speed of response of the element. Unless the element response rate is so raised, the laser pulse light source cannot be made to emit a light pulse at the moment a cell reaches the imaging point 38 following detection of its passage by the position of the triggering light source 32.

The collector lens 50, pin hole 52 and photodiode 54 correspond to a portion of the cell sensor 34 shown in FIG. 1.

Numeral 56 denotes a pulse diode laser. Examples of the pulse diode laser which can be used are the L2376 manufactured by Hamamatsu Photonics (wavelength: 890 nm, power: 10 W) and the GAAP-12 manufactured by Sanders (wavelength: 870-904, power: 12W). A condenser lens 58 forms an enlargement optical system on the side of the image pick-up light source. As shown in FIG. 4, the focal point F of the condenser lens 58 is slightly more distant than the center of the flow cell 18 as seen from the pulse diode laster 56. More specifically, the focal point F is set in such a manner that when a CCD camera 64 takes a picture, a cell image of sufficient size will be obtained within the screen. The distance q from the condenser lens 58 to the focal point F and the distance p from the pulse diode laser 56 to the condenser lens 58 preferably are related by the inequality $q/p \gg 10$.

The pulse diode laser 56 and the condenser lens 58 are substantially equivalent to the image pick-up laser pulse light source 20 and condenser lens 22, respectively, shown in FIG. 1. Numeral 60 denotes means for reducing coherence, such as frosted glass or a bundle of optical fibers. An image pick-up lens 62 employs a microscope objective lens having a magnification of 20 to 40 and corresponds to the objective lens 24 shown in FIG. 1. The image pick-up lens 62 is also positionally adjusted by a fine position adjuster, not shown. Numeral 64 denotes the aforementioned CCD camera.

Figure 5:
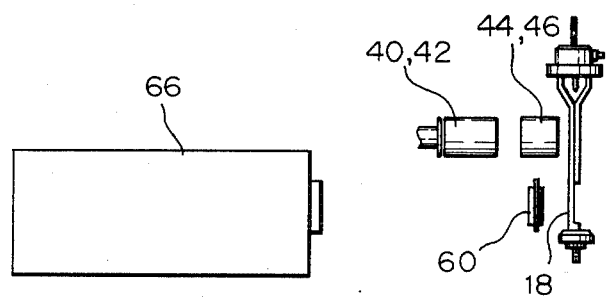
FIG. 5 is a view useful in describing an optical system in an embodiment employing an N2 laser or the like as an image pick-up light source in the apparatus for flow cytometry according to the present invention.

FIG. 5 illustrates an arrangement in which the diode laser 56 of FIG. 2 is replaced by a light source comprising an $N_2$ laser, YAG laser, $N_2$/Dye laser or a combination of a YAG laser and high-frequency oscillator. Since the light from the laser 66 is parallel, the condenser lens 58 of FIG. 2 can be dispensed with and the laser light is incident directly upon the photo cell 18.

Figure 6:
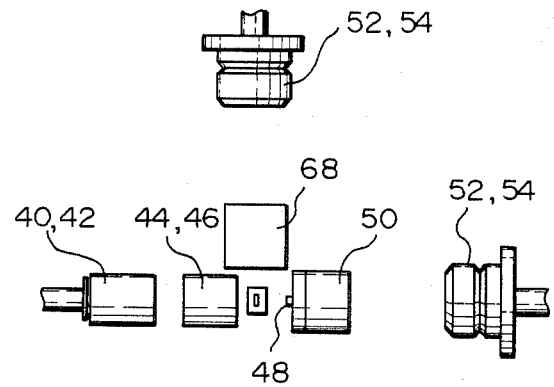
FIG. 6 is a view useful in describing an optical system in which the embodiment of FIG. 2 is additionally provided with a system for detecting side-scattered light.
Figure 7A:
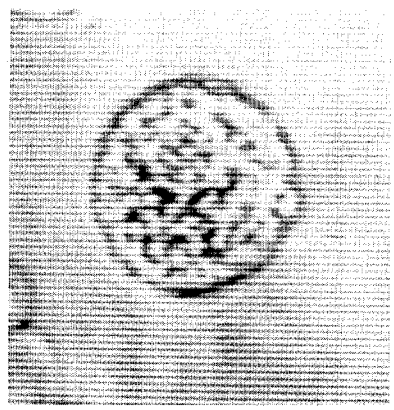
FIGS. 7(a)-(d) are photographs of four groups of white blood cells taken in accordance with the present invention.
Figure 7B:
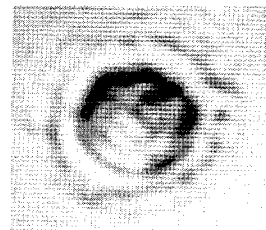
Figure 7C:
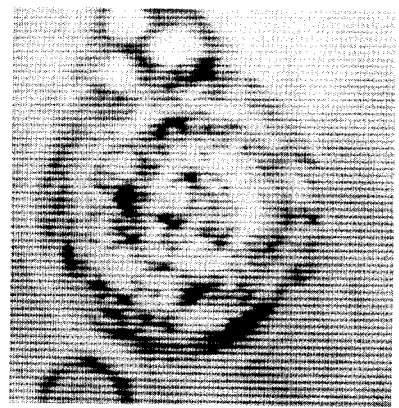
Figure 7D:
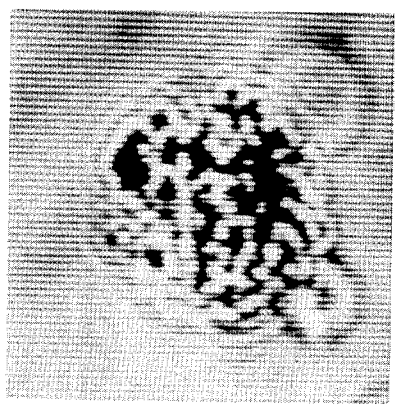

FIG. 6 illustrates an embodiment in which it is arranged to detect side-scattered light in addition to forward-scattered light in order to sense a cell. To this end, there is provided a collector lens 68 for detecting the side-scattered light. By arranging it so that both forward- and side-scattered light are detected, cells are sensed with greater reliability. Another advantage is greater applicability. The reason is that since the side-scattered light is reflective of both cell size and the state of the cell surface or interior, a greater amount of information is obtained in comparison with the case where solely the forward-scattered light, which in the main reflects cell size, is detected. This also makes it possible to detect passage of cells more reliably. Furthermore, whereas cell type cannot be identified based solely on the size of the cell, the fact that information relating to the cell surface or cell interior is obtained makes it possible to accurately determine the type of cell. This also makes it possible to photograph a cell of interest only when this cell passes through the photo cell.

Let us now describe use of a nitrogen laser with regard to the optical resolution of the apparatus 10 and a limitation upon the flow velocity of the sheathed flow for the purpose of obtaining a still picture of a cell.

A nitrogen laser is capable of producing a strong (peak power: 100 KW or more) laser pulse having a wavelength of 337.1 nm and a pulse width of about 10 nS. High-power light having a pulse width as small as this can only be obtained from a laser. In addition, since a nitrogen laser produces ultraviolet light, excellent resolution is obtained, as will be set forth below.

Resolution $\delta$ is decided by the numerical aperture NA of the objective lens and the wavelength $\lambda$ of light, as indicated by the following equation:

$$\delta = \lambda/NA$$

In the present embodiment, the aperture number NA of the objective lens 24 is 0.85, so that the resolution $\delta$ is about 0.4 μm, i.e., $\delta = \lambda/NA = 337.1/0.85 = 396.6$ nm.

Since the pulse width $\Delta x$ of a nitrogen laser is about 10 nS and the resolution is about 0.4 μm, the maximum velocity v of the sheathed flow at which a still picture of cell can be obtained is found as follows:

$$v = \delta/\Delta x = 0.40 \times 10^{-6}/10 \times 10^{-9} = 40 \text{ m/S}$$

Thus, a still can picture of a cell can be obtained if the cells flow through the flow cell at a velocity of not more than about 40 m/s. However, since the sheathed flow will develop a disturbance if the flow velocity is too high, the velocity must be held below about 6 m/s in actual practice.

Let us now describe an example in which the flow cytometry apparatus 10 of the invention is used to photograph white blood cells of a healthy individual and to divide the white blood cells into groups based on the picture obtained.

First, the white blood cells are stained in such a manner that the state of granulation within the cells can be readily identified. The staining method is characterized in that collected blood is stained while still living, as opposed to a method in which dried blood is stained.

The staining of the cells and the method of dilution is as follows:

a. A Giemsa diluent is prepared by adding one drop of stain to 1 cc of distilled water.

b. The Giemsa diluent and undiluted blood are mixed at a ratio of 4:1 and staining is carried out for 30 min under occasional stirring.

A specimen prepared by the above method (hereafter referred to as "supravital staining") is allowed to flow into the apparatus 10 from the inlet 14. The image of the blood cells during their passage by the imaging point 38 is picked up by the CCD camera 26 and transmitted to the system control and picture processing unit 30 through the still picture input unit 28. The processing unit 30 processes the still picture to remove flicker and noise.

Pictures of white blood cells obtained in the aforementioned manner are divided into four groups. Table I shows the characteristics and the occurrence rate of each group, and (a) through (d) in FIG. 7 illustrate the pictures of the four groups. Groups A, C and D have a dimension of about 30 μm on one side of the picture, while the similar dimension in group B is about 15 μm.

TABLE I

| GROUP | DIAMETER (μm) | Characteristics of White Blood Cell Pictures Obtained by Flow Method STATE OF GRANULATION | APPEARANCE RATE % |
|---|---|---|---|
| Group A | 12-17 | Small in size, large in number | 63.2 |
| Group B | 7-14 | Not found | 28.0 |
| Group C | 16-21 | Not found | 7.2 |
| Group D | 16-17 | Large in size and number | 1.6 |

The pictures of the white blood cells were compared by microscopic observation with specimens stained with a May-Giemsa composite stain or with specimens prepared by placing blood stained with a supravital stain on glass slides which were then provided with cover glasses. As a result of these observations, Group A was identified as being composed of neutrophils, Group B of lymphocytes, Group C of monocytes and Group D of eosinophils and basophils.

Accordingly, with the apparatus for flow cytometry of the illustrated embodiment, white blood cells are photographed and the pictures of white blood cells obtained are analyzed to ascertain the size and the granulation of the white blood cells, thereby enabling these white blood cells to be classified and identified by type based on the characteristics given in Table I.

Figure 8:
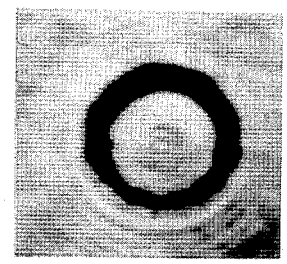
FIG. 8 is a photograph of a red blood cell taken in accordance with the present invention.

FIG. 8 illustrates a picture of a red blood cell photographed during its flow through the flow cell used in the apparatus of the illustrated embodiment. The ring-shaped stripes encircling the red blood cell in FIG. 8 are diffraction rings caused by the red blood cell. If the diffraction rings are an impediment to picture analysis of the red blood cell, the coherence of the laser light should be reduced to weaken the diffraction phenomenon. An appropriate expedient for accomplishing this is to dispose a sheet of glass between the condenser lens 22 and the flow cell 18.

As many apparently widely different embodiments of the present invention can be made without departing from the spirit and scope thereof, it is to be understood that the invention is not limited to the specific embodiments thereof except as defined in the appended claims.

What is claimed is:

1. An apparatus for flow cytometry comprising:
   a flow cell through which a sheathed stream flows;
   a triggering light source which continuously emits a light beam on the sheathed stream;
   a cell sensor for generating a cell detection signal upon sensing that a cell has traversed the light beam from said triggering light source;
   a delay circuit for transmitting the cell detection signal to an image pick-up laser pulse light source after delaying the cell detection signal for a fixed period of time;
   said image pick-up laser pulse light source emitting a pulse of laser light onto the flow cell to illuminate the cell sensed by the cell sensor;
   a condenser lens for condensing laser light emitted by said image pick-up laser pulse light source;
   means arranged downstream of said condenser lens and immediately upstream from said flow cell for reducing the coherence of the laser light emitted onto the flow tube from said image pick-up laser pulse light source;
   an objective lens and a CCD camera for taking a still picture of cells flowing through the sheathed stream when the cells are illuminated by the pulse of laser light condensed by said condenser lens; and
   a picture processor for processing and analyzing the still picture obtained.

2. The apparatus according to claim 1, wherein said cell sensor generates said cell detection signal in accordance with the size of the cell traversing the light beam.

* * * * *